(12) United States Patent
Villette

(10) Patent No.: US 7,591,807 B2
(45) Date of Patent: Sep. 22, 2009

(54) PENETRATING INJECTION NEEDLE

(76) Inventor: Alain Villette, Les Vannes, 79700 Saint-Pierre les Echaubrognes (FR)

( * ) Notice: Subject to any disclaimer, the term of this patent is extended or adjusted under 35 U.S.C. 154(b) by 0 days.

(21) Appl. No.: 11/455,938

(22) Filed: Jun. 20, 2006

(65) Prior Publication Data
US 2007/0021725 A1 Jan. 25, 2007

(30) Foreign Application Priority Data
Jun. 20, 2005 (FR) .................... 05 06215

(51) Int. Cl.
*A61M 5/32* (2006.01)
(52) U.S. Cl. .................. 604/272; 604/264
(58) Field of Classification Search ............ 604/272, 604/274; 606/80; 433/165
See application file for complete search history.

(56) References Cited
U.S. PATENT DOCUMENTS

| | | | |
|---|---|---|---|
| 3,308,822 A | 3/1967 | De Luca | |
| 3,788,320 A * | 1/1974 | Dye | 604/165.04 |
| 4,490,139 A | 12/1984 | Huizenga et al. | |
| 5,820,609 A | 10/1998 | Saito | |
| 5,938,635 A * | 8/1999 | Kuhle | 604/506 |
| 5,968,022 A * | 10/1999 | Saito | 604/272 |
| 2005/0107751 A1* | 5/2005 | Yatabe et al. | 604/272 |
| 2005/0234386 A1 | 10/2005 | Nishikawa et al. | |

FOREIGN PATENT DOCUMENTS

| | | |
|---|---|---|
| EP | 1 506 791 | 2/2005 |
| FR | 2 481 930 | 12/1984 |
| GB | 748451 | 5/1956 |
| WO | WO 2004/006996 | 2/2004 |

* cited by examiner

*Primary Examiner*—Nicholas D Lucchesi
*Assistant Examiner*—Laura A Bouchelle
(74) *Attorney, Agent, or Firm*—Leydig, Voit & Mayer, Ltd.

(57) ABSTRACT

A penetrating injection needle for the injection of a pharmaceutical product into a human or animal body. The needle includes a tubular body having two opposing ends, a first end for connection to a device for driving the needle in rotation and pumping a product, and a second end for penetration of the human or animal body and including a main bevel and at least one secondary bevel. The secondary bevel or bevels is/are arranged in opposition relative to the main bevel and form a cutting edge and a needle point with the main bevel.

22 Claims, 3 Drawing Sheets

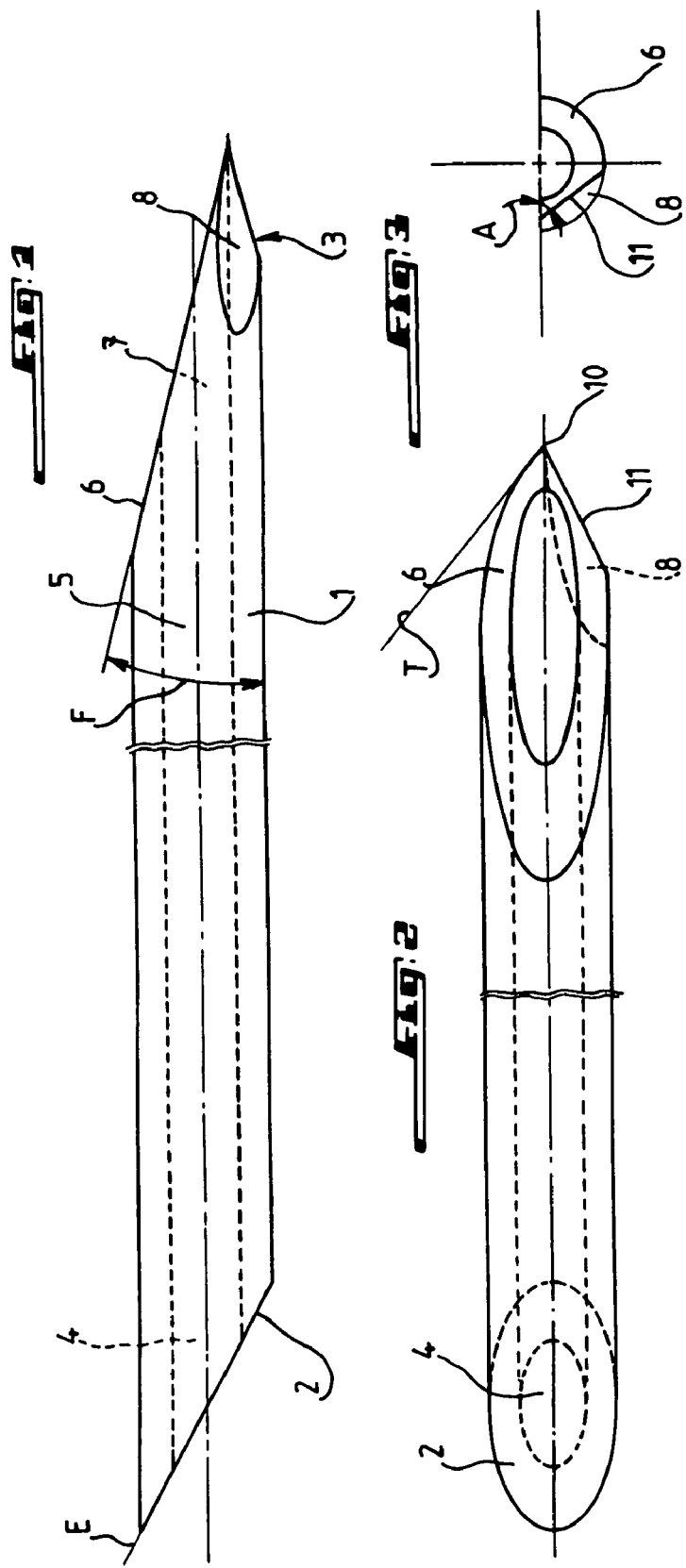

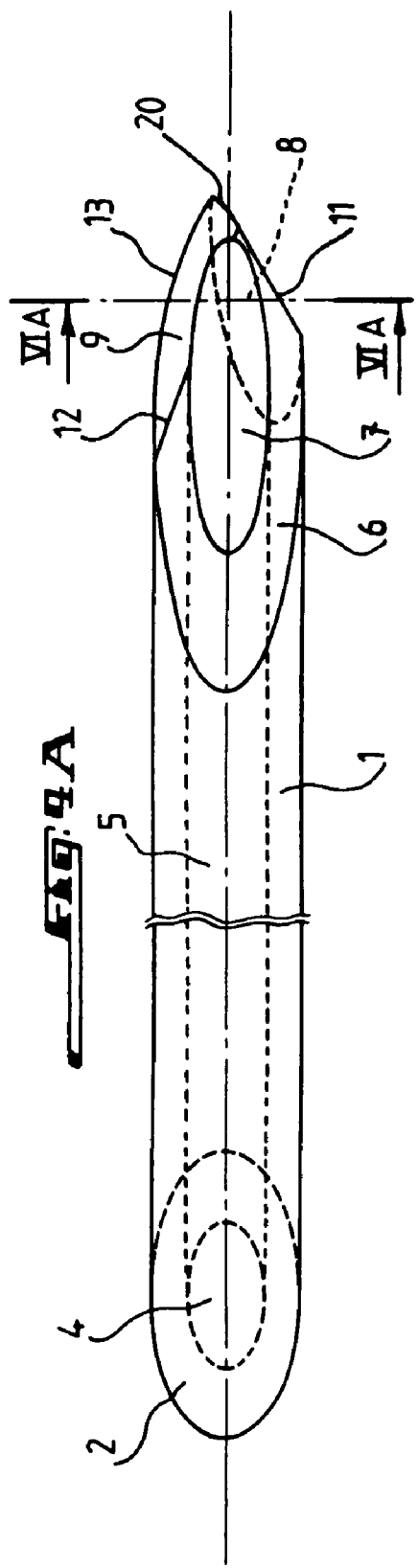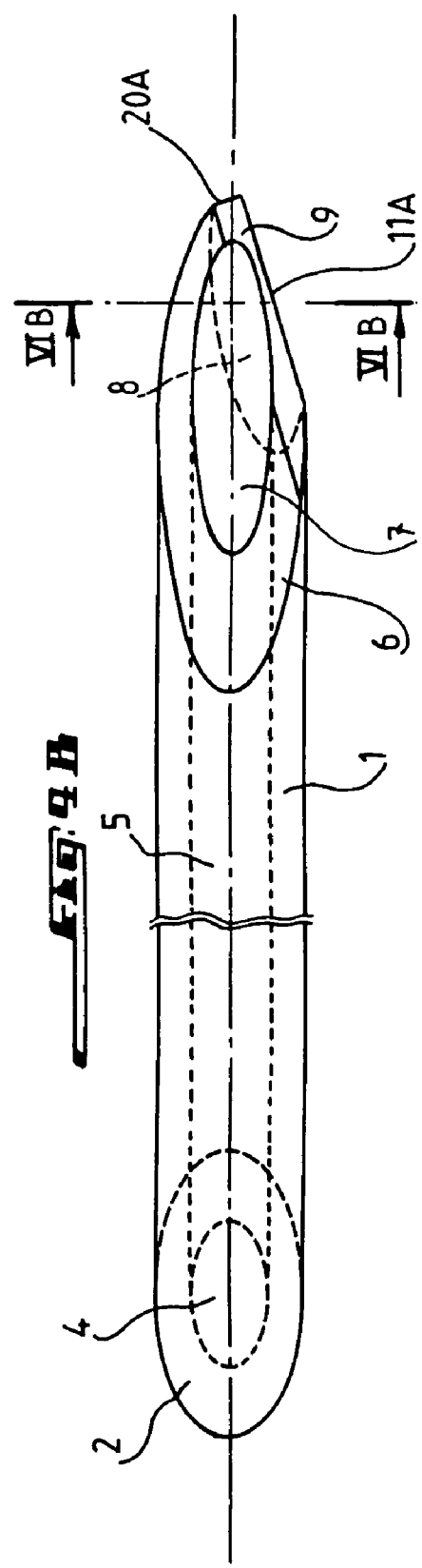

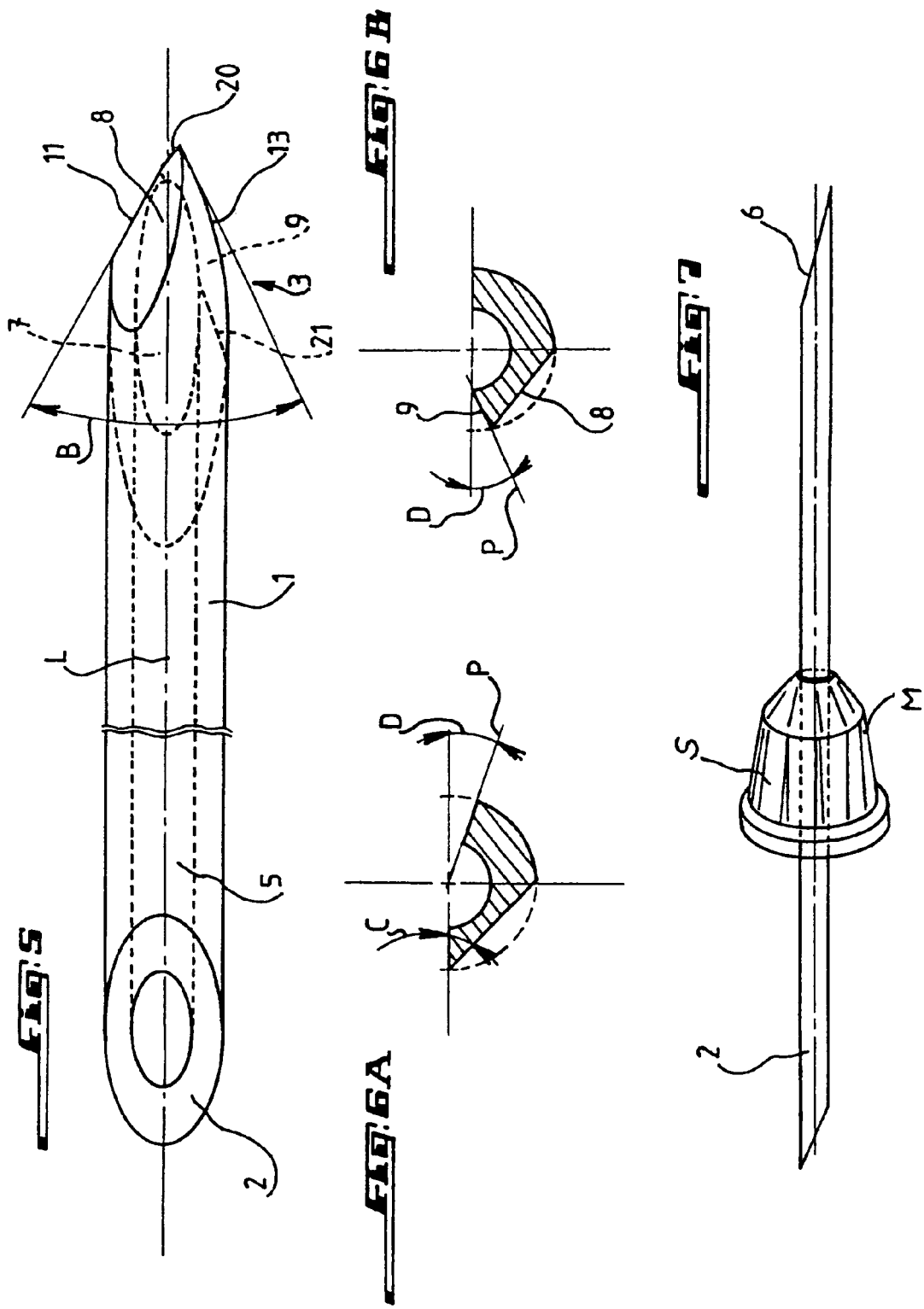

PENETRATING INJECTION NEEDLE

FIELD OF THE INVENTION

The invention concerns a penetrating injection needle for the injection of a pharmaceutical product into a hard tissue of the human or animal body and for a less painful injection in the case of injection into a soft tissue.

BACKGROUND

During dental care it is necessary to administer a local anesthesia to the patient. This injection is usually given in the gums and produces effects in the surrounding soft tissues. Aside from the discomfort that this represents for the patient, the efficacy of the anesthesia is not always optimal. This is essentially due to the fact that the anesthetic product partially diffuses away from the tooth being treated instead of remaining concentrated.

During dermatological treatment of man or animal, it is sometimes also useful to have a needle in order to perform a less painful or safer injection.

On certain needles, in order for the practitioner to work with precision, the base or connecting part of the needle, which may be made of plastic or metal and permits the needle to be screwed into the syringe, has a marking which indicates the positioning of the main bevel of the needle. Ordinarily the mark is on the side of the bevel, which means that when one views the needle from the side, one sees the mark and the main bevel at the same time.

However, this positioning of the mark does not permit the practitioner to use the bevel correctly, since the main bevel should be situated flatly on the mucosa or skin for a painless injection. The practitioner should therefore make certain that the needle is always turned in such a way that the mark is not visible, which does not correspond to accurate positioning but to a highly approximate positioning.

In order to alleviate the various problems described above, penetrating injection needles have been developed so as to make it possible, e.g., for the dentist to penetrate to the interior of the bone mass where the teeth are situated and deposit the anesthetic there. Therefore, the latter is deposited in the spongy interdental bone, resulting in immediate anesthesia of the teeth to be treated. The bone is surrounded by a cortical, i.e. a hard part forming a casing; the liquid anesthetic is less subject to the phenomenon of migration, which is not the case in a peripheral tissue irrigated by the blood. For the dermatologist and veterinarian the needles with a more cutting bevel permit the painless penetration of the surface layers of the skin.

The perforating injection needles were developed from the commonly used injection needles. Therefore, these perforating injection needles consist of a tubular body having two opposite ends, of which a first end provided with a single short bevel (posterior) is intended to be connected to means for driving in rotation and means for supplying or dispensing of the liquid. It is in reference to this bevel, during the fabrication, that the marking is positioned on the base, permitting the marking of the anterior bevel. The second end which is intended to penetrate into the human or animal body is provided with a long (anterior) bevel, constituting the main bevel which is supplemented by the other two bevels, the secondary bevels. According to the description, the main bevel specifies the face before the second end of the needle.

Now the second ends of the needles with their three bevels basically have one or another of two forms. According to the first form, which is the most widespread, the two secondary bevels are situated on the plane surface of the main bevel. They make the needle more pointed. This is the "lancet" bevel. According to the second form, less widespread than the first, the two secondary bevels are situated opposite the main bevel and therefore form counter-bevels. This arrangement of the three bevels gives the point of the needle a pyramid shape. This is the "back cut" bevel.

During use, in rotation, for a perforation by a needle having one or another of the arrangements of the triple bevel described above, the penetrating power into the bone mass is mediocre.

In addition, such injection needles have a point angle of the order of 60 degrees. The main bevel has an angle relative to the longitudinal axis of the needle of the order of 10 and 15 degrees.

However, in the course of various practical uses it has been found that these injection needles displace the tissues when an injection is made into the gingiva. The penetration is therefore quite painful. Moreover, these needles suffer from the fact that the angles formed by the intersection of the bevels between themselves or the bevels and the circular wall are close to or even greater than 60 degrees.

SUMMARY OF THE INVENTION

The objective of the invention is to propose a penetrating injection needle that is free of the shortcomings described above.

The goal of the invention is achieved with a penetrating needle for injection of a pharmaceutical product into a human or animal body which consists of a tubular body having two opposing ends, i.e. a first end intended to be connected to means for driving it in rotation and means for pumping the product and also designed to permit the correct positioning of the mark on the anterior bevel on the base, a second end intended to penetrate into the human or animal body and provided for that purpose with a main bevel and at least one secondary bevel.

According to the invention, the second end of the needle is provided with a secondary bevel that is arranged in opposition to the main bevel and forms with the latter a cutting edge and a needle point.

The fact that the needle of the invention is provided with a cutting edge means especially, in contrast with needles having two counter bevels, that the needle is especially designed for perforation and incision, a task which involves a first incision for starting a removal of tissue and then a cutting of the tissue in slices in order to accomplish the removal of the tissue, the incision and cutting being realized by the cutting edge of the needle which has the geometric characteristics that were studied especially for this task.

In fact, as opposed to counter-bevel needles, which essentially displace the tissue into which they penetrate, the needle of the invention cuts the tissue in the direction of the cut, i.e. following a helical motion with a significant circumferential component corresponding to the speed of rotation of the needle and a much less significant axial component corresponding to the speed of penetration—or axial speed—of the needle. This incision of the tissue is performed continually to the degree that the cutting edge of the needle progresses and permits removal of the tissue in the form of slices thus trimmed off.

This manner of moving the needle of the invention is equally applicable to soft tissue, e.g., during a dermatological treatment and to hard tissue, e.g., in a dental treatment.

According to a first mode of realization the perforating needle of the invention has only a secondary bevel and a single cutting edge as described above.

According to a second mode of realization, the perforating needle of the invention has a first secondary bevel and a second secondary bevel. The first secondary bevel corresponds, in its design and the role to be played, to the single secondary bevel of the first mode of realization. It is therefore arranged opposite the main bevel and forms a cutting edge with it. The second secondary bevel is arranged opposite the first secondary bevel and adjacent to the main bevel on a plane inclined relative to the main bevel and forms a edge with the main bevel and, with the periphery of the tubular body, an auxiliary cutting edge whose angle varies along the edge of the needle. The main bevel and the two secondary bevels together form a needle point in the form of a flat blade.

The needle in the second mode of realization may also have at least one of the characteristics below, considered in isolation or in any technically possible combination.

- the second secondary bevel is inclined relative to the main bevel at an inclination angle of the order of 15 degrees;
- the cutting edge and the auxiliary cutting edge enclose between them a point angle of the order of 70 to 80 degrees;
- the main bevel forms with the longitudinal axis of the tubular body an angle of the order of 10 to 20 degrees;
- the base of the needle is provided with a mark for positioning arranged opposite the main bevel, with respect to the longitudinal axis of the needle.

Thanks to the asymmetrical arrangement of the secondary bevels and more particularly thanks to the fact that the perforating injection needle of the invention has only a single cutting edge, the needle performs better in perforating and cutting soft tissues, making it less painful. Generally speaking, the end of a needle is always formed by the intersection of a plane and a tube at a certain angle and by the intersection of one or another planes that may surround the axis of the tube and form with the first plane an edge of a constant angle (cutting or trimming edge) and with the edge of the tube an edge whose angle is variable.

A mathematical calculation permits calculation of the angles formed by the intersections as a function of the angles of rotation of the different planes and thus the adaptation of the needle to the function it is supposed to perform.

Other characteristics and advantages of the present invention will emerge from the following description of the two modes of realization, which description refers to the drawings.

BRIEF DESCRIPTION OF DRAWING FIGURES

In the drawings:

FIG. 1 shows a perforating needle according to the invention in a side view, FIG. 2 shows a perforating needle according to a first mode of realization of the invention in a view of the main bevel of the needle, FIG. 3 shows a transverse section of the perforating needle of FIG. 2, FIGS. 4A and 4B show a perforating needle according to a second mode of realization of the invention and a variant in a view toward the main bevel of the needle, FIG. 5 shows the face opposite the main bevel of the needle of FIG. 4, FIGS. 6A and 6B show a cross section of the perforating needle of FIG. 4A and FIG. 4B, and FIG. 7 shows a needle according to the invention with a support bearing a marking.

DETAILED DESCRIPTION

A perforating injection needle according to the invention such as is represented, e.g., on FIGS. 1 and 7, consists of a tubular body 1 having two opposite ends 2 and 3. The first end 2 is designed to be connected by way of a support or base S of plastic, to the means for driving in rotation and to the means for pumping liquid, in this case a pharmaceutical liquid such as, e.g., an anesthetic liquid or a liquid for dermatological treatment. The liquid is introduced into the injection needle through an inlet 4 of a channel 5 passing through the entire length of the needle. The orientation of the bevel determines the marking of the needle; it should therefore be parallel to the main bevel described below.

The second end 3 of the needle is provided with a main bevel 6 and an opening 7 of the channel 5. The second end 3 is intended to penetrate into a hard or soft tissue in which the liquid is to be deposited. While the first end 2 includes a short bevel inclined at an angle E of approximately 20 to 25 degrees relative to a longitudinal axis L of the needle, the second end 3 displays a long bevel; the main bevel 6 of this end is inclined at an angle F of approximately 10 to 20 degrees relative to the longitudinal axis L of the needle.

According to a first mode of realization of the invention shown in FIGS. 2 and 3, the perforating injection needle is provided at the second end 3 with a secondary bevel 8 arranged opposite the main bevel 6 and forming with it a cutting edge 11 and a needle point 10. The main bevel 6 and the secondary bevel 8 enclose between themselves on the one hand a cutting angle A of the order of 40 degrees and on the other hand a point 10. This point may be moved laterally relative to the axis in order to cause the angle of the point B, measured between the cutting edge 11 and the tangent T to the edge of the main bevel 6 adjacent to the cutting edge 11, to vary between approximately 30 and 40 degrees.

According to a second mode of realization of the invention, shown in FIGS. 4A, 5 and 6A, the perforating injection needle is provided at the second end 3 with two secondary bevels, a first secondary bevel 8 and a second secondary bevel 9. The first secondary bevel 8 is arranged opposite the main bevel 6 and forms a cutting edge 11 with it. The second secondary bevel 9 is arranged adjacent to the main bevel 6 on a plane P inclined at an angle D of 20 to 35 degrees relative to the main bevel 6 and forms with the main bevel 6 an edge 12 and with a part of the circumference of the tubular body 1 opposite the main bevel 6 an auxiliary cutting edge 13. The main bevel 6 and the two secondary bevels 8,9 together form a needle point in the form of a flat blade 20 resulting from the intersection of the two secondary bevels 8,9 with the image of a scalpel blade.

In addition, the secondary bevels 8,9 are oriented in such a way that a single one of these two bevels, in the mode of realization represented, the secondary bevel 8, forms with the main bevel 6 a cutting edge 11 or else these two bevels together may be reversed relative to the axis of the needle in order to make reverse rotation possible.

However, as a variant, it is equally possible that the second secondary bevel 9 is arranged on the side opposite the main bevel 6 and that it forms with the first secondary bevel 8 a cutting edge 11A and a blade 20A (FIG. 4B). In this variant, the plane P is then arranged on the other side of the axis L (FIG. 6B).

The first and the second secondary bevels 8, 9 form between themselves a point angle B corresponding to that of the first mode of realization and which is therefore of the order of 35 to 45 degrees. The two secondary bevels 8,9 are also arranged in such a way that the secondary bevel 8 or 9 which forms the cutting edge 11 with the main bevel 6 forms with the main bevel 6 an angle C of the order of 40 degrees.

The two secondary bevels 8, 9 are also arranged asymmetrically relative to a median plane of the needle passing through a longitudinal axis L of the needle, this median plane rising perpendicularly relative to the plane of the drawing. Therefore, the two secondary bevels 8, 9 are arranged in such a way that they rejoin uniquely to form the point 20 in the form of a flat blade.

The penetration capacity of the needle of the invention does not depend only on the arrangement of the secondary bevels 8, 9 relative to the main bevel 6; it is interesting to recall that the main bevel 6 forms with the longitudinal axis L of the tubular body 1 of the needle in each of the two modes of realization an angle of the order of 10 to 20 degrees.

To facilitate the positioning of the injection needle according to the invention in the means for driving it in rotation or in a needle holder combining the functions of driving and pumping liquid, the needle according to the invention is provided with a positioning mark M realized as a mark engraved on the base S of plastic or metal. The mark M is situated on the back of the needle relative to the main bevel 6. This permits the practitioner to know that the main bevel 6 of the needle is fully parallel to the mucosa.

The invention claimed is:

1. A penetrating injection needle for the injection of a pharmaceutical product into tissue, the needle comprising:
   a tubular body having a longitudinal axis lying in a first plane; and
   a pointed end, the pointed end consisting of
      a main bevel having a planar main bevel surface lying in a second plane, wherein the second plane is perpendicular to the first plane and the main bevel surface is oblique to the longitudinal axis, and
      a first secondary bevel having a planar first secondary bevel surface lying in a third plane, opposite the second plane, that intersects the first and second planes, and that is oblique to the first and second planes, the third plane intersecting the second plane at an intersection forming a single continuous linear cutting edge that ends at a needle point of the needle.

2. The needle as in claim 1, wherein the second plane and the third plane enclose between themselves a wedge angle at the single cutting edge of approximately 40 degrees.

3. The needle as in claim 1, wherein the needle point has a point angle defined by the second plane and the third plane and in a range from 30 to 40 degrees.

4. The needle as in claim 1, wherein the second plane intersects the longitudinal axis at an angle in a range of 10 to 20 degrees.

5. The needle as in claim 1, wherein the needle point is asymmetrical with respect to the first plane.

6. A penetrating injection needle for the injection of a pharmaceutical product into tissue, the needle comprising:
   a tubular body having a longitudinal axis lying in a first plane; and
   a pointed end, the pointed end consisting of
      a main bevel having a planar main bevel surface lying in a second plane, wherein the second plane is perpendicular to the first plane and the main bevel surface is oblique to the longitudinal axis,
      a first secondary bevel having a planar first secondary bevel surface lying in a third plane, opposite the second plane, that intersects the first and second planes, and that is oblique to the first and second planes, the third plane intersecting the second plane at an intersection forming a single continuous linear cutting edge that ends at a needle point of the needle, and
      a second secondary bevel adjacent the main bevel, the second secondary bevel having a planar second secondary bevel surface lying in a fourth plane that is inclined relative to the second plane and forming, at an intersection with the second plane, an edge, and forming, with a part of the tubular body, at an intersection with the second plane, an auxiliary cutting edge.

7. The needle as in claim 6, wherein the second secondary bevel is inclined relative to the second plane by an angle of inclination of approximately 35 degrees.

8. The needle as in claim 6, wherein the single linear cutting edge and the auxiliary cutting edge form an acute angle in a range of 35 to 45 degrees.

9. The needle as in claim 6, wherein the first and second secondary bevels are asymmetrical relative to the first plane.

10. The needle as in claim 6, wherein the second plane intersects the first plane at an angle in a range of 10 to 20 degrees.

11. The needle as in claim 6, wherein the needle point lies outside the first plane.

12. The needle as in claim 6, wherein the first and second secondary bevels intersect at the needle point along the linear cutting edge.

13. A penetrating injection needle for the injection of a pharmaceutical product into tissue, the needle comprising:
   a tubular body having a longitudinal axis lying in a first plane; and
   a pointed end, the pointed end consisting of
      a main bevel having a main bevel surface lying in a second plane, wherein the second plane is perpendicular to the first plane and the main bevel surface is oblique to the longitudinal axis,
      a first secondary bevel having a planar first secondary bevel surface lying in a third plane, opposite the second plane, the third plane being oblique to the first and second planes and intersecting the first and second planes, and
      a second secondary bevel having a planar second secondary bevel surface lying in a fourth plane that intersects the second plane at a first intersection and that intersects the third plane at a second intersection, the second intersection forming a single continuous cutting edge that ends at a needle point of the needle.

14. The needle as in claim 13, wherein the first and second secondary bevels are asymmetrical relative to the first plane.

15. The needle as in claim 13, wherein the second plane intersects the first plane at an angle in a range of 10 to 20 degrees.

16. The needle as in claim 13, wherein the needle point is asymmetrical with respect to the first plane.

17. The needle as in claim 13, wherein the needle point lies outside the first plane.

18. A penetrating injection needle for the injection of a pharmaceutical product into tissue, the needle comprising:
   a tubular body having a longitudinal axis lying in a first plane; and
   a pointed end, the pointed end consisting of
      a main bevel having a main bevel surface lying in a second plane, wherein the second plane is perpendicular to the first plane and the main bevel surface is oblique to the longitudinal axis, a first secondary bevel having a planar first secondary bevel surface lying in a third plane, opposite the second plane, the third plane being oblique to the first and second planes and intersecting the first and second planes, and a second secondary bevel having a planar second secondary bevel surface lying in a fourth plane that intersects the second plane at a first intersection and that intersects the third plane at a second intersection, the second intersection forming a single continuous cutting edge that ends at a needle point of the needle.

19. The needle as in claim 18, wherein the first and second secondary bevels are asymmetrical relative to the first plane.

20. The needle as in claim 18, wherein the needle point is asymmetrical with respect to the first plane.

21. The needle as in claim 18, wherein the needle point lies outside the first plane.

22. The needle as in claim 18, wherein the first intersection forms a second linear cutting edge.

* * * * *